(12) United States Patent
Chen et al.

(10) Patent No.: US 6,674,030 B2
(45) Date of Patent: Jan. 6, 2004

(54) INTELLIGENT SURGICAL FOOTPEDAL WITH LOW NOISE, LOW RESISTANCE VIBRATION FEEDBACK

(75) Inventors: Jerry S. J. Chen, Orange, CA (US); Dung Ma, Santa Ana, CA (US)

(73) Assignee: Advanced Medical Optics, Santa Ana, CA (US)

( * ) Notice: Subject to any disclaimer, the term of this patent is extended or adjusted under 35 U.S.C. 154(b) by 203 days.

(21) Appl. No.: 09/957,091

(22) Filed: Sep. 19, 2001

(65) Prior Publication Data

US 2003/0051985 A1 Mar. 20, 2003

(51) Int. Cl.[7] .................................................. H01H 3/14
(52) U.S. Cl. ....................... 200/86.5; 200/61.29; 74/512
(58) Field of Search ..................... 200/86.5, 61.29, 200/61.89, 51 LM; 74/512

(56) References Cited

U.S. PATENT DOCUMENTS

| | | | |
|---|---|---|---|
| 4,333,070 A | | 6/1982 | Barnes |
| 4,354,071 A | | 10/1982 | Pietschmann ............. 200/86.5 |
| 4,888,997 A | * | 12/1989 | Eckert et al. ............ 73/862.65 |
| 4,983,901 A | * | 1/1991 | Lehmer ..................... 318/685 |
| 5,039,973 A | * | 8/1991 | Carballo ..................... 338/153 |
| 5,091,656 A | * | 2/1992 | Gahn ......................... 307/119 |
| 5,247,218 A | * | 9/1993 | Sven ........................... 310/81 |
| 5,268,624 A | | 12/1993 | Zanger |
| 5,382,891 A | * | 1/1995 | Huffener ..................... 318/269 |
| 5,787,760 A | | 8/1998 | Thorlakson |
| 5,983,749 A | | 11/1999 | Holtorf |
| 6,150,623 A | | 11/2000 | Chen |

FOREIGN PATENT DOCUMENTS

| | | | |
|---|---|---|---|
| DE | 3741246 A1 | 6/1989 | |
| FR | 2646545 | 4/1989 | ........... G08C/17/00 |
| WO | WO 93/02627 | 2/1993 | ........... A61B/17/20 |

* cited by examiner

*Primary Examiner*—Lincoln Donovan
*Assistant Examiner*—K. Lee
(74) *Attorney, Agent, or Firm*—Walter A. Hackler; Peter Jon Gluck

(57) ABSTRACT

A surgical footpedal includes a treadle size for receiving a user's foot and adapted for enabling depression thereof in order to activate signals for control of associated surgical apparatus. A vibrator is disposed on the treadle for vibrating the treadle at selected treadle depressions to provide sensory warning to the user that further treadle depression will cause a given event to occur. A bracket is provided for attaching the vibrator to the treadle for causing resonant vibration of the treadle and the vibrate.

23 Claims, 2 Drawing Sheets

INTELLIGENT SURGICAL FOOTPEDAL WITH LOW NOISE, LOW RESISTANCE VIBRATION FEEDBACK

The present invention relates generally to medical apparatus; more particularly, to foot-operated controls for surgical apparatus. Numerous type of apparatus include as part of the apparatus, a connected, hand-held medical implement or tool. Operation of the tool requires control of various operating parameters or functions.

An example of such medical apparatus, is a phacoemulsifier apparatus which is especially constructed for surgically removing the natural, crystalline lenses from cataract eyes in preparation for the insertion of an artificial intraocular lens. Phacoemulsifier apparatus typically comprise a cabinet, which contains a power supply, vacuum pump, electronic, and associated hardware, and a connected multifunction, hand-held surgical implement having a slender hollow needle-like tube which is inserted into a patients eye in order to perform the phacoemulsion operation.

Functions of the phacoemulsifier hand-held surgical implement include irrigating the eye (with a saline solution), ultrasonically emulsifying (disintegrating) the eye lens, aspirating (by vacuum) the emulsified lens, cauterizing broken blood vessels, and vitretomy (removing vitreous humor from the eye). It can be appreciated that a surgeon using the hand-held implement to perform such functions requires the ability to control these functions, as well as the ability to selectively shift or switch between at least some of the functions (for example, irrigation and irrigation pulse aspiration) as the need arises during phacoemulsion surgery.

It should be appreciated that complete controlling and/or shifting of functions of a phacoemulsification handpiece from a remote, cabinet-mounted controls is generally unsatisfactory. Normally, a surgeon using the handpiece is too involved in the medical procedure to be able to operate remotely located, cabinet-mounted controls. On the other hand, having an attendant operate the cabinet-mounted controls is even less practical except, perhaps, for simple medical procedures and apparatus.

Such problems associated with adjusting cabinet-mounted controls while operating an associated hand-held medical implement may be overcome, in some simple cases, by mounting controls directly on the hand-held implement. This may, for example, be satisfactory when the only control required is to turn a function performed by the hand-held implement on and off and/or to vary an operational speed of a function performed by the implement. Then, included on the implement of a ON/OFF microswitch perhaps with the additional inclusion of speed control, may be feasible for some medical apparatus. However, phacoemulsification procedures performed by a skilled surgeon requires extremely precise control and, therefore, attempting to control a function with the same hand that is simultaneously manipulating the hand-held implement to perform a delicate operation is generally not preferred.

As an alternative (or a supplement) to cabinet-mounted and/or hand-held implement-mounted controls foot controls are frequently provided for medical (and other) apparatus, thereby freeing an operator's hands so that he or she can concentrate on manipulating hand-held implement. Some such foot pedal controls, for example, have heretofore used one or more electrical switches mounted along the path of pedal movement so as to enable one or more operational functions to be respectively turned on and off by the operator depressing and releasing the foot pedal. In addition or alternatively, electric potentiometers have heretofore been connected to the pedal to enable the varying of an operational function by analog means according to the angle through which the pedal is displaced by the operator.

Mechanical detents are also known to have been used for providing increased resistance to angular pedal movement at preestablshed detent points, thereby providing a sensory warning to the operator that slightly further pedal depressing will cause a given event to occur. For example, such detents may be used to alert the operator to the turning off of one operational function and the turning on of another function by a control switch or switches mounted in the path of pivotal pedal movement.

This warning, or indication, is important in phacoemulsification surgery where various sequences of operations are required, such as, for example:

i) irrigation of the eye with a saline solution;
ii) a combination of simultaneous irrigation and aspiration of the irrigating fluid; and
iii) a combination of fluid irrigation and phacoemulsification power on the patient.

The footpedal may be used to control a function by a range of deflection or depression and to switch between functions by further depression. It is, of course, important that the operating surgeon be made aware of the switch, or transistor points.

Heretofore, the most commonly used tactile footpedal feedback is a clutch device controlled by a steppermotor. The motor exercises a torque when the footpedal is entering a specified a zone, or degree of depression. Thus, the surgeon will feel additional resistance at this point. Unfortunately, when the surgeon encounters additional torque at the transition zone, the physician will naturally exercise more torque which may cause premature entry into another function, or zone of operation.

An alternative method to provide feedback is through the use of a solenoid which is installed under the pedal. When the pedal is depressed at a transition point, the solenoid is powered to tap the footpedal. This has the advantage of providing no additional resistance to the pedal depression. However, this feedback system has a number of disadvantages. Namely, the vibration typically is noisy due to metal-to-metal contact which is unfavorable in a quiet operating room environment. Further, exercising the solenoid requires additional electrical power which may not be suitable for an intelligent footpedal with firmware incorporated. For example, see U.S. Pat. No. 4,983,901. Footpedals must be designed in accordance with safety regulation which requires them to sustain forces of 300 lbs/per square inch. This requirement requires a heavy mass which requires larger size solenoids and tremendous electrical power supply.

The present invention provides for improved sensory warning to a surgeon when utilizing a foot pedal requiring depression thereof to change operation or function at specific depressions, or transition points.

SUMMARY OF THE INVENTION

A surgical footpedal in accordance with the present invention generally includes a treadle size for receiving a user's foot and adapted for enabling depression thereof in order to activate signals of control of associated surgical apparatus.

A vibrator is provided and disposed on the treadle for vibrating the treadle at selected treadle depression in order to provide sensory warning to the user that further treadle depression will cause a given event or occur.

A bracket attaches the vibrator to the treadle and causes resonant vibration of the treadle and the vibrator. This resonant operation is important in that it enables a very small vibrator, preferably an electric motor having a rotatable shaft and an eccentric weight attached to the shaft, to be utilized.

Preferably, the vibrator is disposed on an underside of the treadle and a bracket attaching the vibrator to the treadle underside, has an hourglass shape. That is, bracket is formed from elongate strip having a waist portion which is narrow than end portions of the strip.

The vibrator is attached to the bracket at the waist portion and the bracket is attached to the treadle proximate the end portions of the strip. In causing resonant vibration of the pedal and vibrator, the bracket thus functions as a vibrational, or mechanical or amplifier. This is important in view of the fact that the footpedal may have a weight exceeding 1.02 kilograms while the vibrator may weigh less than 6.5 grams. Thus, the weight of the treadle is at least about 31 times the total weight of the vibrator and the bracket.

The footpedal is adapted for depression through the use of a hinge for pivotally attaching the treadle to a base. The vibrator is disposed in a spaced apart relationship with the hinge and may be surrounded by a wall projecting from the treadle underside. A removable cover is provided for enclosing a wall, vibrator and the bracket in order to prevent environmental exposure. Preferably the treadle is angulated and the vibrator is disposed at an intersection of the angulated portions.

BRIEF DESCRIPTION OF THE DRAWINGS

The advantage and features of the present invention will be better understood by the following description when considered in conjunction with the accompanying drawings, in which.

DETAILED DESCRIPTION

Figure 1:
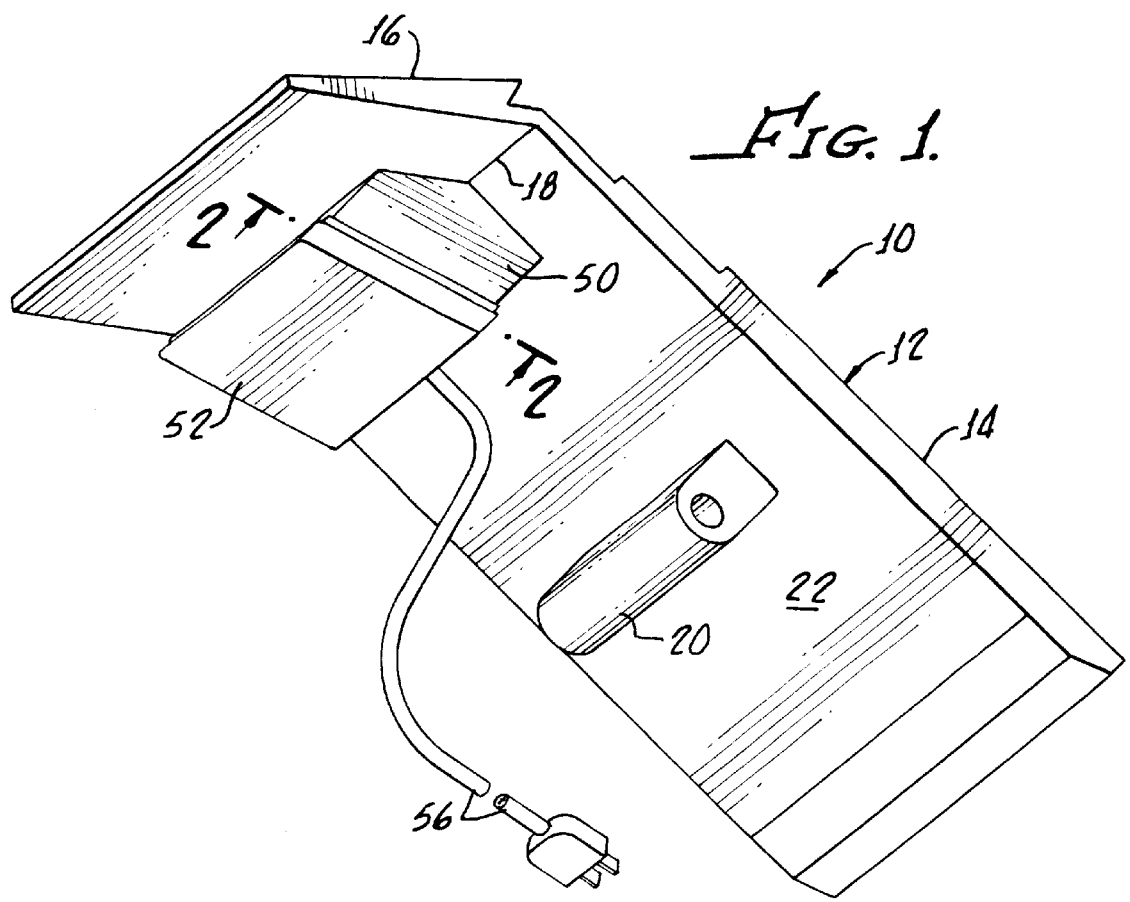
FIG. 1 is a perspective view of a footpedal in accordance with the present invention showing an underside of treadle with a covered wall for enclosing a vibrator.

With reference to FIG. 1, there is shown a footpedal 10 in accordance with the present invention which generally includes a treadle 12 which is sized for receiving a user's foot (not shown). The treadle 12 may be angulated having a sole portion 14 for receiving a user's foot and a toe portion 16 for receiving a user's toe, the two portions having a line of intersection 18. This dual use arrangement is shown in U.S. Pat. No. 6,150,623 and is to be incorporated herewith in its entirety by this specific reference thereto. A hinge 20 may be attached or formed into a underside 22 of the treadle 12 for enabling mounting of the treadle 12 to a base, not shown.

The pivotal mounting of the treadle 12 enables depression thereof in order to activate signals for control of assorted surgical apparatus (not shown). Operation of the footpedal 10 in this regard is generally described in U.S. Pat. Nos. 4,983,901 to Lehmer and 6,150,623 to Chen. These patents are to be incorporated into the present application in their integrity for describing the general operation of the footpedal 10.

Figure 2:
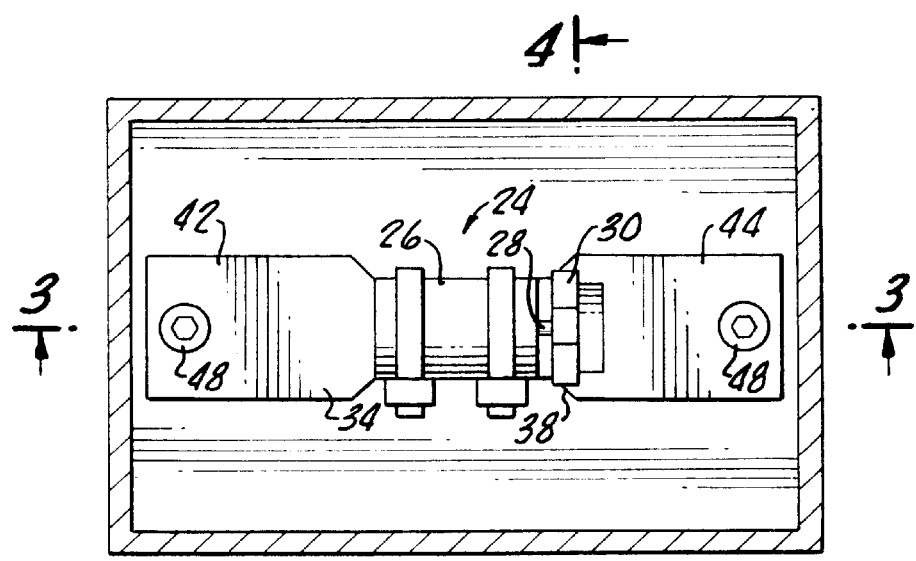
FIG. 2 is a plan view of a vibrator in accordance with the present invention which includes an electric motor, an eccentric weight and tuning bracket.
Figure 3:
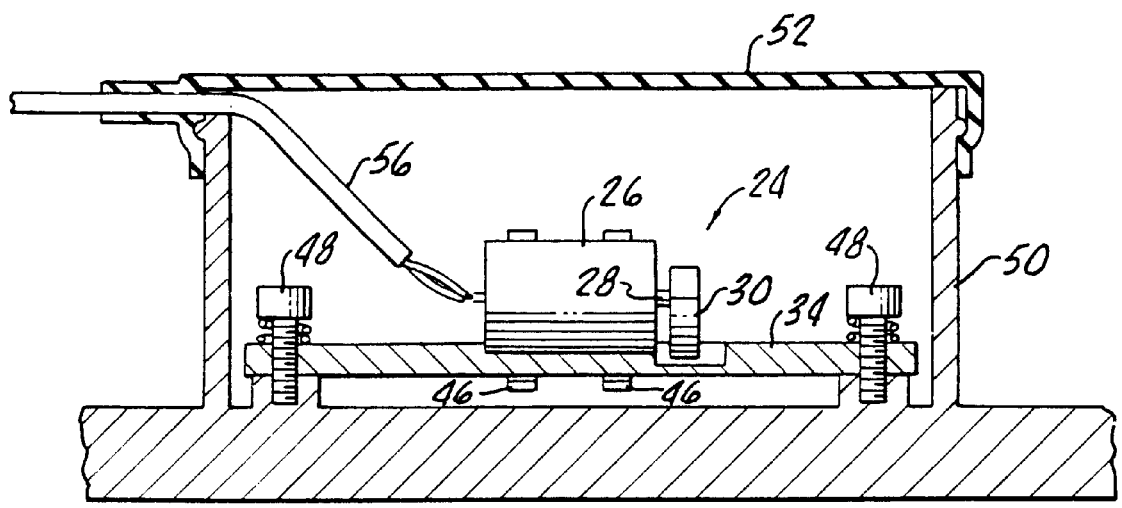
FIG. 3 is a cross-sectional view taken along the line 3—3 of FIG. 2.
Figure 4:
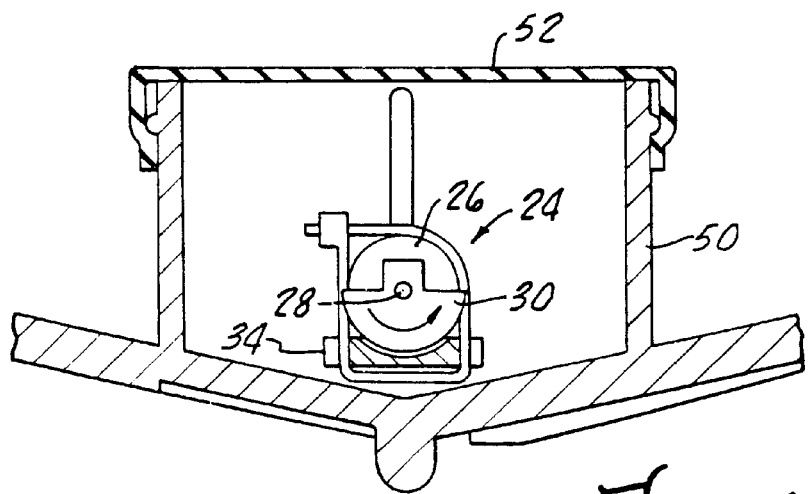
FIG. 4 is a cross-sectional view taken along the line 4—4 of FIG. 2.

With reference also to FIGS. 2–4, a vibrator 24 is disposed on the treadle underside 22 for vibrating the treadle at selected treadle 12 depression to provide sensing warning to the user that further treadle 12 depression will cause a given event to occur. This operation is described in the hereinabove referenced patents.

Preferably, the vibrator 24 includes a miniature electric motor 26 having a rotating shaft 28 with an eccentric weight 30 fixed thereto. A suitable motor is sold by Gin Long Machinery & Electronic Company Ltd., Wenzhou China, under the model number OTL-10BL. This motor 26, is of very light weight, or example, about 6.5 grams that consumes little power. Accordingly, the motor 26 may be battery powered or used in a computer output circuit.

A footpedal treadle 12 is of significant mass in order to sustain foot loading but also to meet safety regulations which dictate support of 300 lbs/per sq inch. Thus, it must be appreciated that the treadle 12 has significant mass, in fact, greater than about 1.02 kilograms.

In order to provide a sensor warning to the user through the user's foot with the use of the light weight motor 26, a resonating bracket 34 is provided for attaching the vibrator motor 26 to the treadle underside 18. The shape of the bracket 34, being generally an hourglass and formed from a metal strip with a waist portion 38 having a narrower width than end portions 42, 44 of the strip bracket 34 (See FIG. 2).

The motor 26 is fixed to the waist portion 38 by screws 46 or the like and the bracket ends 42, 44 are attached to the treadle underside 18 by screws 48 or the like. Thus, the motor 26 and eccentric weight 30 are suspended from the treadle underside. In addition, it is preferable to attach the vibrator 24 at toe and side portion intersection 18 not only to enhance resonant coupling but to ensure that the vibrational warning is served by the user whether the user is depressing the toe portion 16 or the sole portion 14 of the treadle 12.

Utilizing a footpedal having a longitudinal dimension of about 26 centimeters and a width of about 11 centimeters with a thickness of about 5 to 10 millimeters and formed from a metal such as Aluminum 356, the bracket 34, which may be formed from Stainless Steel 316 has a length of about 6 to 7 centimeters, a maximum width of about 7–10 millimeters and a waist width of about 0.4 inches. In this configuration, the weight of the treadle is at least 31 times the total weight of the vibrator 24 and bracket 34. The bracket 34 also serves as a heat sink for the motor 26.

To further enhance resonant operation of the footpedal 10, and provide protection to the vibrator 22, a wall 50 may be attached or formed in the treadle underside 22 surrounding the vibrator 24. This wall also enables the use of a removable cover 52 formed in plastic or the like, for enclosing the wall 50, vibrator 24 and bracket 34 from the environmental exposure. The wall also contributes to the resonant frequency and adds to distribute vibration to the toe portion 16 and sole portion 14.

In operation, the vibrator motor 26, is activated through electrical lines 56 connected to a console, not shown, for vibrating the treadle 12 at selected treadle depressions to provide sensing warning to the user. Such controlled depressions and activation points are described in the hereinabove referenced U.S. patents.

Although there has been hereinabove described a specific arrangement of a surgical pedal in accordance with the present invention, for the purpose of illustrating the manner in which the invention may be used to advantage, it should be appreciated that the invention is not limited thereto.

Accordingly, any or all modifications, variations, or equivalent arrangements which may occur to those skilled in the art should be considered to be within the scope of the present invention as defined in the appended.

What is claimed is:

1. A surgical footpedal comprising:
   a treadle for receiving a user's foot and for enabling depression thereof in order to activate signals for control of associated surgical apparatus;
   a vibrator, disposed on said treadle, for vibrating said treadle at selected treadle depressions to provide sensory warning to the user that further treadle depression will cause a given event to occur; and
   a bracket, attaching said vibrator to said treadle, for causing resonant vibration of said treadle and said vibrator.

2. The footpedal according to claim 1 wherein said vibration comprises an electric motor having a rotatable shaft and an eccentric weight attached to the shaft.

3. The footpedal according to claim 1 wherein said vibration is disposed on an underside of said treadle.

4. The footpedal according to claim 3 further comprising a wall surrounding said vibrator and said bracket, said wall projecting from the treadle underside.

5. The footpedal according to claim 4 further comprising a removable cover for enclosing said wall, vibration and bracket in order to prevent environmental exposure thereto.

6. The footpedal according to claim 1 wherein said bracket has an hourglass shape.

7. The footpedal according to claim 1 wherein said bracket comprises an elongate strip having a wrist portion narrower than end portions, of the strip.

8. The footpedal according to claim 7 wherein said vibrator is attached to said bracket at the waist portion and said bracket is attached to said treadle proximate the end portions of the strip with the motor suspended from said treadle.

9. The footpedal according to claim 1 wherein said treadle is angulated having a sole portion for receiving a user's foot and a toe portion for receiving a user's toe, the toe and sole portion having a line of intersection and said vibrator is disposed along said line of intersection.

10. The footpedal according to claim 1 wherein a weight of said treadle is up to about 31 times a total weight of said vibrator and said bracket.

11. The footpedal according to claim 10 wherein said treadle and said bracket are comprised of metal for providing a heat sink for said electrical motor.

12. The footpedal according to claim 1 wherein the treadle comprises a hinge for pivotally attaching said treadle to a base and said vibrator is disposed in a spaced apart relationship with said hinge.

13. A surgical footpedal comprising:
    a frame for receiving a user's foot and for enabling depression thereof in order to activate signals for control of associated apparatus;
    a vibrator disposed on said frame for vibrating said frame at selected intervals to alert the user of selected indications, said vibration comprising an electrical motor having a rotatable shaft and an eccentric weight attached to the shaft; and
    a bracket, attaching said vibrator to said frame, for enabling resonant vibration of said frame and said vibrator.

14. The footpedal according to claim 13 wherein said vibrator is disposed on an underside of said treadle.

15. The footpedal according to claim 14 further comprising a wall surrounding said vibrator and said bracket, said wall projection from the treadle underside.

16. The footpedal according to claim 15 further comprising a removable cover for enclosing said wall, vibrator and bracket in order to prevent environmental exposure thereto.

17. The footpedal according to claim 13 wherein said bracket has an hourglass shape.

18. The footpedal according to claim 13 wherein said bracket comprises an elongate strip having a wrist portion narrower than end portions of the strip.

19. The footpedal according to claim 18 wherein said vibration is attached to said bracket at the wrist portion and said bracket is attached to said treadle proximate the end portions of the strip.

20. The footpedal according to claim 13 wherein said treadle is angulated having a sole portion for receiving a user's foot and a toe portion for receiving a user's foot and toe portion for receiving a user's toe, the toe and sole portion having a line of intersection and said vibrator is disposed along said line of intersection.

21. The footpedal according to claim 13 wherein a weight of said treadle is at least about 31 times the total weight of said vibrator and said bracket.

22. The footpedal according to claim 13 wherein the treadle comprises a hinge for pivotally attaching said treadle to a base and said vibrator is disposed in a spaced apart relationships with said hinge.

23. The footpedal according to claim 21 wherein said treadle and said bracket are composed of metal for providing a heat sink for said electrical mater.

* * * * *